(12) United States Patent
Themelis

(10) Patent No.: US 11,588,986 B2
(45) Date of Patent: Feb. 21, 2023

(54) APPARATUSES, METHODS, AND COMPUTER PROGRAMS FOR A MICROSCOPE SYSTEM FOR OBTAINING IMAGE DATA WITH TWO FIELDS OF VIEW

(71) Applicant: Leica Instruments (Singapore) Pte. Ltd., Singapore (SG)

(72) Inventor: George Themelis, Lindau (DE)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 17/167,495

(22) Filed: Feb. 4, 2021

(65) Prior Publication Data

US 2021/0243387 A1    Aug. 5, 2021

(30) Foreign Application Priority Data

Feb. 5, 2020    (EP) ..................................... 20155554

(51) Int. Cl.
*H04N 5/272*    (2006.01)
*G02B 21/00*    (2006.01)
(Continued)

(52) U.S. Cl.
CPC ......... *H04N 5/272* (2013.01); *G02B 21/0012* (2013.01); *G02B 21/367* (2013.01); *H04N 5/2258* (2013.01)

(58) Field of Classification Search
CPC ........ A61B 2090/364; A61B 2090/365; A61B 2090/371; A61B 90/20; G02B 21/0012;
(Continued)

(56) References Cited

U.S. PATENT DOCUMENTS 10,659,848 B1 *    5/2020  Baughman .........  G06K 9/00369
2004/0070822 A1     4/2004  Shioda et al.
(Continued)

FOREIGN PATENT DOCUMENTS

CN    102809808 A    12/2012
EP       3151720 A1     4/2017
(Continued)

*Primary Examiner* — James T Boylan
(74) *Attorney, Agent, or Firm* — 2SPL Patent Attorneys PartG mbB; Kieran O'Leary

(57) ABSTRACT

Examples relate to apparatuses, methods and computer programs for a microscope system, more specifically, but not exclusively, to the use of two optical imaging modules to obtain image data having a first and a second field of view. The apparatus comprises an interface. The interface is suitable for obtaining first image data of a sample from a first optical imaging module. The first image data has a first field of view. The interface is suitable for obtaining second image data of the sample from a second optical imaging module. The second image data has a second field of view. The first field of view comprises the second field of view. The apparatus comprises a processing module. The processing module is configured to generate an image output signal for a display of the microscope system. In some embodiments, the processing module is configured to process the first image data to detect an abnormality outside the second field of view. In this case, information on the abnormality is overlaid over the second image data within the image output signal. Additionally or alternatively, an overview of the first image data is overlaid over the second image data within the image output signal. The processing module is configured to provide the image output signal to the display.

15 Claims, 4 Drawing Sheets

(51) Int. Cl.
*G02B 21/36* (2006.01)
*H04N 5/225* (2006.01)

(58) Field of Classification Search
CPC .............. G02B 21/0016; G02B 21/367; H04N 5/2258; H04N 5/272
See application file for complete search history.

(56) References Cited

U.S. PATENT DOCUMENTS

| | | | |
|---|---|---|---|
| 2008/0104116 A1* | 5/2008 | Van Hoe | G06T 7/0012 |
| 2010/0283842 A1* | 11/2010 | Guissin | G02B 27/144 |
| | | | 348/68 |
| 2012/0112751 A1* | 5/2012 | Littmann | G01R 33/4838 |
| | | | 324/322 |
| 2014/0066700 A1 | 3/2014 | Wilson et al. | |
| 2014/0118551 A1* | 5/2014 | Ikeda | B60R 1/00 |
| | | | 348/148 |
| 2014/0160264 A1* | 6/2014 | Taylor | A61F 9/008 |
| | | | 348/79 |
| 2014/0375683 A1* | 12/2014 | Salter | G02B 27/0172 |
| | | | 345/633 |
| 2015/0145950 A1* | 5/2015 | Murphy | H04N 5/23238 |
| | | | 348/36 |
| 2015/0256768 A1* | 9/2015 | Dolgin | H04N 5/2258 |
| | | | 348/164 |
| 2016/0133011 A1* | 5/2016 | Nakajima | G06T 7/0012 |
| | | | 382/128 |
| 2016/0203263 A1* | 7/2016 | Maier | G06T 7/0016 |
| | | | 705/2 |
| 2017/0270715 A1* | 9/2017 | Lindsay | G06T 7/70 |
| 2017/0359512 A1* | 12/2017 | Mojaver | H04N 5/232 |
| 2019/0151024 A1* | 5/2019 | Abraham | A61B 34/25 |
| 2019/0324252 A1* | 10/2019 | Mak | H04N 5/232 |
| 2019/0391012 A1* | 12/2019 | Kokota | G02B 7/38 |
| 2020/0382725 A1* | 12/2020 | Gao | H04N 5/23218 |

FOREIGN PATENT DOCUMENTS

| | | |
|---|---|---|
| EP | 3575847 A1 | 12/2019 |
| JP | 2017038285 A | 2/2017 |
| WO | 2018221041 A1 | 12/2018 |

* cited by examiner

APPARATUSES, METHODS, AND COMPUTER PROGRAMS FOR A MICROSCOPE SYSTEM FOR OBTAINING IMAGE DATA WITH TWO FIELDS OF VIEW

CROSS-REFERENCE TO A RELATED APPLICATION

This application claims priority to European Application 20155554.7, filed on Feb. 5, 2020. The content of this earlier filed application is incorporated by reference herein in its entirety.

TECHNICAL FIELD

Examples relate to apparatuses, methods and computer programs for a microscope system, more specifically, but not exclusively, to the use of two optical imaging modules to obtain image data having a first and a second field of view.

BACKGROUND

In general, a microscope is an optical instrument that is suitable for examining objects that are too small to be examined by the human eye (alone). For example, a microscope may provide an optical magnification of an object, such as a sample of organic tissue. Observation through the microscope eyepiece may thus provide a high magnification image of a very narrow field of view. For example, in surgical microscopes, the narrow field of view may lead to a reduction of awareness over the broader surgical cavity, and the patient overall. The surgeon might be temporarily unaware of events, such as bleeding. To mitigate such situations, the surgeon may remove the eyes from the eyepiece and look with the naked eye. However, this may lead to a loss of focus, and might not be performed as often as desired.

In JP 2017 038285 A, a medical treatment observation device is shown, which uses a first and a second imaging section for imaging a first and a second visual field. Images of the first and second visual field can be shown alternatingly on the same display device, using different display devices, or using different regions of the same display device.

SUMMARY

There may be a desire for an improved concept for the perception of a sample in a microscope system, which allows for an improved awareness of the surgeon towards incidents outside a magnified field of view of the microscope system.

This desire is addressed by the subject-matter of the independent claims.

Embodiments are based on the finding, that incidents in an area that surrounds the magnified field of view of a camera can be visualized within the same display that is being used to view the magnified view of a sample being viewed through the microscope. This is implemented by using image data of two optical imaging modules, one having a first (wider) field of view, and the other having a second (narrower) field of view, the first field of view encompassing the second field of view. In some embodiments, the incidents may be visualized by detecting an abnormality within the wider field of view and providing a visual indication that is overlaid over the narrower field of view on the display. In some other embodiments, the incidents may be visualized by overlaying an overview of the wider field of view over a portion of the narrower field of view on the display. In both cases, the user of the microscope (i.e., the operator of the microscope, such as a surgeon) is enabled to detect anomalous incidents within the wider field of view without abandoning their focus on the narrower field of view, increasing their awareness of incidents occurring within the wider field of view.

Embodiments of the present disclosure provide an apparatus for a microscope system. The apparatus comprises an interface for obtaining first image data of a sample from a first optical imaging module. The first image data has a first field of view. The interface is suitable for obtaining second image data of the sample from a second optical imaging module. The second image data has a second field of view. The first field of view comprises the second field of view. The apparatus comprises a processing module configured to process the first image data to detect an abnormality outside the second field of view. The processing module is configured to generate an image output signal for a display of the microscope system. Information on the abnormality is overlaid over the second image data within the image output signal. The processing module is configured to provide the image output signal to the display. By overlaying the information on the abnormality over the second image data, the user of the microscope (i.e., the operator of the microscope, such as a surgeon) is enabled to detect anomalous incidents within the wider field of view without abandoning his/her focus on the narrower field of view, increasing the awareness of incidents occurring within the wider field of view.

For example, the display may be an ocular display of an eyepiece of the microscope system. In other words, the user/surgeon may be notified of the abnormality within the display of the eyepiece, enabling the user/surgeon to keep focused on the sample.

In various embodiments, the sample is a sample of organic tissue of a surgical site. The processing module may be configured to detect bleeding outside the second field of view. Information on the bleeding may be overlaid over the second image data. Consequently, the surgeon may be made aware of the bleeding while using the surgical microscope to magnify a part of the surgical site.

For example, information on a location of the bleeding may be overlaid over the second image data. This may enable the surgeon to navigate to the source of the bleeding, either with the microscope or by leaving the microscope and focusing on the bleeding without the help of the microscope.

In some embodiments, the sample is a sample of material to be inspected. The processing module may be configured to detect an irregularity within the material outside the second field of view. Information on the irregularity may be overlaid over the second image data. This may enable a spot-check of materials without losing sight of irregularities being present outside the spots being used for the spot check.

An overview of the first image data may be overlaid over the second image data if an abnormality is detected outside the second field of view. This may alert the user/surgeon of the abnormality and provide the user with information on the location of the abnormality.

For example, a location of the abnormality may be highlighted in the overview of the first image data. This may provide the user with information on the location of the abnormality, which may improve a reaction time required for reacting to the abnormality.

In some embodiments, the interface is suitable for obtaining further image data from one or more further optical imaging modules. The processing module may be configured to detect an abnormality within the further image data.

Information on the abnormality within the further image data may be overlaid over the second image data within the image output signal. This may make the user of the microscope system aware of incidents that occur around the sample.

Embodiments of the present disclosure further provide a further apparatus for a microscope system. The apparatus comprises an interface for obtaining first image data of a sample from a first optical imaging module. The first image data has a first field of view. The interface is further suitable for obtaining second image data of the sample from a second optical imaging module. The second image data has a second field of view, the first field of view comprising the second field of view. The apparatus comprises a processing module configured to generate an image output signal for a display of the microscope system. An overview of the first image data is overlaid over the second image data within the image output signal. The processing module is configured to provide the image output signal to the display. By overlaying the first image data over the second image data, the user of the microscope (i.e., the operator of the microscope, such as a surgeon) is enabled to monitor incidents within the wider field of view without abandoning his/her focus on the narrower field of view, increasing the awareness of incidents occurring within the wider field of view.

Again, the display may be an ocular display of an eyepiece of the microscope system. In other words, the user/surgeon may be notified of the abnormality within the display of the eyepiece, enabling the user/surgeon to keep focused on the sample.

For example, the sample may be a sample of organic tissue of a surgical site. The first image data may comprise an overview of the surgical site. The second image data may comprise a magnified view of a portion of the surgical site. The overview of the surgical site may be overlaid over a portion of the magnified view. Consequently, the surgeon may be made aware of the incidents outside the magnified view, such as bleeding, while using the surgical microscope to observe the magnified view.

In some embodiments, the interface is suitable for obtaining a trigger signal from an input device of the microscope system. The processing module may be configured to generate the image output signal such that the overview of the first image data is overlaid over the second image data within the image output signal in response to the trigger signal of the input device. Using the trigger signal, the user/surgeon may choose when to display the first image data, e.g., in order to selectively overlay it over the second image data, or in order to temporarily remove the overlay.

For example, a location of the second field of view within the first field of view may be highlighted within the overview of the first image data. This may provide the user with information on the relative location of the two fields of view, and thus improve a spatial awareness of the user.

In various embodiments, the interface is suitable for obtaining a steering signal from an input device of the microscope system. The interface may be suitable for providing a control signal for a robotic adjustment system of the microscope system. The processing module may be configured to control the robotic adjustment system based on the steering signal. A change of the location of the second field of view within the first field of view may be highlighted within the overview of the first image data. This may provide the user with information on the relative location of the two fields of view as the second field of view is being moved, and thus improve a spatial awareness of the user.

Embodiments further provide a microscope system, such as surgical microscope system, comprising at least one of the apparatuses. By including the apparatus within the microscope system, the user of the microscope system may be enabled to monitor incidents within the wider field of view without abandoning his/her focus on the narrower field of view, increasing the awareness of incidents occurring within the wider field of view.

Embodiments of the present disclosure further provide an embodiment of a method for a microscope system. The method comprises obtaining first image data of a sample from a first optical imaging module. The first image data has a first field of view. The method comprises obtaining second image data of the sample from a second optical imaging module. The second image data has a second field of view. The first field of view comprises the second field of view. The method comprises processing the first image data to detect an abnormality outside the second field of view. The method comprises generating an image output signal for a display of the microscope system. Information on the abnormality is overlaid over the second image data within the image output signal. The method comprises providing the image output signal to the display.

Embodiments of the present disclosure further provide a further embodiment of a method for a microscope system. The method comprises obtaining first image data of a sample from a first optical imaging module. The first image data has a first field of view. The method comprises obtaining second image data of the sample from a second optical imaging module. The second image data has a second field of view. The first field of view comprises the second field of view. The method comprises generating an image output signal for a display of the microscope system. An overview of the first image data is overlaid over the second image data within the image output signal. The method comprises providing the image output signal to the display.

Embodiments of the present disclosure further provide a computer program with a program code for performing at least one of the embodiments of the method when the computer program is executed on a processor.

SHORT DESCRIPTION OF THE FIGURES

Some examples of apparatuses and/or methods will be described in the following by way of example only, and with reference to the accompanying figures, in which.

DETAILED DESCRIPTION

Various examples will now be described more fully with reference to the accompanying drawings in which some examples are illustrated. In the figures, the thicknesses of lines, layers and/or regions may be exaggerated for clarity.

Figure 1A:
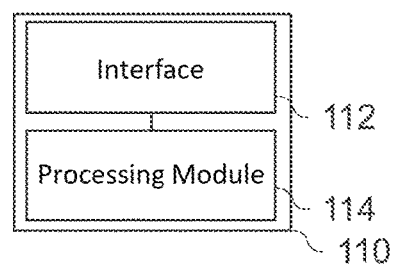
FIGS. 1a and 1b show block diagrams of embodiments of an apparatus for a microscope system and of a microscope system, respectively.
Figure 1B:
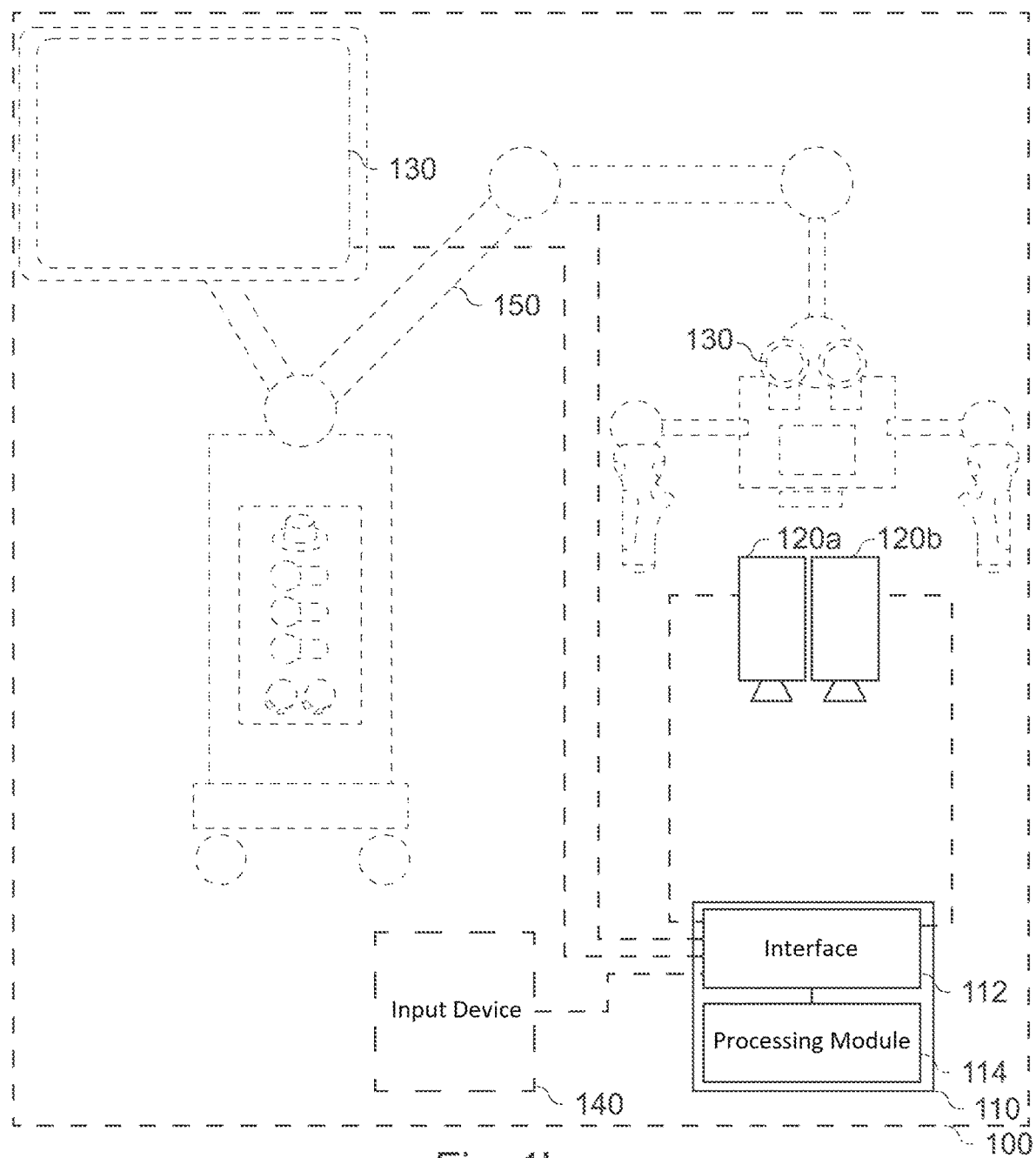

FIGS. 1a and 1b show block diagrams of embodiments of an apparatus 110 for a microscope system and of a microscope system 100, respectively. The apparatus 110 comprises an interface 112. The interface 112 is suitable for (e.g., configured to) obtaining/obtain first image data of a sample from a first optical imaging module 120a. The first image data has a first field of view. The interface 112 is suitable for (e.g., configured to) obtaining/obtain second image data of the (same) sample from a second optical imaging module 120b. The second image data has a second field of view. The first field of view comprises the second field of view. The apparatus 110 comprises a processing module 114, which is coupled to the interface 112. The processing module is configured to obtain the first and second image data from the first and second optical imaging module 120a; 120b, respectively. The processing module is further configured to generate an image output signal for a display 130 of the microscope system. In some embodiments, the processing module 114 is configured to process the first image data to detect an abnormality outside the second field of view. In this case, information on the abnormality may be overlaid over the second image data within the image output signal. Additionally or alternatively, an overview of the first image data is overlaid over the second image data within the image output signal. The processing module 114 is configured to provide the image output signal to the display 130 (via the interface 112).

FIG. 1b shows a block diagram of an embodiment of the microscope system 100. The microscope system 100 comprises the apparatus 110, the first and second optical imaging modules 120a; 120b and the display 130, which are coupled to the processing module 114 of the apparatus 110 via the interface 112 of the apparatus 110. Optionally, the microscope system 100 comprises an input device 140, one or more further optical imaging modules, and/or a robotic adjustment system 150, which are also coupled to the processing module 114 of the apparatus 110 via the interface 112 of the apparatus 110.

Embodiments of the present disclosure relate to apparatuses, method and computer programs for a microscope system. In general, a microscope is an optical instrument that is suitable for examining objects that are too small to be examined by the human eye (alone). For example, a microscope may provide an optical magnification of an object, such as the sample mentioned above. In modern microscopes, the optical magnification is often provided for a camera or an imaging sensor, such as the first and/or second optical imaging modules of the microscope system of FIG. 1b. The microscope system 100 may further comprise one or more optical magnification components that are used to magnify a view on the sample. In the context of this application, the term "microscope system" is used, in order to cover the portions of the system that are not part of the actual microscope (which comprises optical components), but which are used in conjunction with the microscope, such as the display and the apparatus.

If the microscope system is used in the medical or biological fields, the object may be a sample of organic tissue, e.g., arranged within a petri dish or present in a part of a body of a patient. For example, the microscope system 100 may be a microscope system for use in a laboratory, e.g., a microscope that may be used to examine the sample of organic tissue in a petri dish. Alternatively, the microscope 100 may be part of a surgical microscope system, e.g., a microscope to be used during a surgical procedure. Although embodiments are described in connection with a microscope system, they may also be applied, in a more general manner, to any optical device. For example, the microscope system may be a system for performing material testing or integrity testing of materials, e.g., of metals or composite materials. In this case, the sample may be a sample of material to be inspected using the microscope system.

In the present disclosure, first and second image data of the first and second optical imaging module are used. In general, the first and second optical imaging modules may each be or comprise one or more optical (still image or video) camera sensors for generating the first or second image data. For example, each optical imaging module may comprise an APS (Active Pixel Sensor)- or a CCD (Charge-Coupled-Device)-based imaging sensor. For example, in APS-based imaging sensors, light is recorded at each pixel using a photodetector and an active amplifier of the pixel. APS-based imaging sensors are often based on CMOS (Complementary Metal-Oxide-Semiconductor) or S-CMOS (Scientific CMOS) technology. In CCD-based imaging sensors, incoming photons are converted into electron charges at a semiconductor-oxide interface, which are subsequently moved between capacitive bins in the imaging sensor modules by a control circuitry of the sensor imaging module to perform the imaging. In embodiments, separate optical imaging modules are used to generate the first and second image data. In other words, the first and second image data may originate from mutually different imaging sensors.

The first and second image data have a different field of view—the first image data has a first field of view, and the second image data has a second field of view, with the first field of view comprising the second field of view. In other words, the first field of view encompasses the second field of view, such that the second field of view covers (only) a portion of the first field of view. The first field of view is also larger than the second field of view. In the context of the microscope system, the terms "wider field of view" or "narrower field of view" may be used. For example, the first image data may have a wider field of view (i.e., the first field of view), and the second image data may have a narrower field of view (i.e., the second field of view). For example, the first field of view may be at least twice (or at least five times, at least ten times, at least 20 times, at least 50 times, at least 100 times) as large (i.e., cover at least 2×/5×/10×/20×/50×/100× the area) as the second field of view. The second, or narrower, field of view may be obtained through the magnification provided by the optical components of the microscope. In other words, the second field of view may be a magnified field of view, and the first field of view may be an un-magnified, or overview, field of view. Accordingly, the first imaging sensor module may be arranged in parallel to the optical components of the microscope of the microscope systems, while the second imaging sensor module may be arranged such, that they employ the optical components of the microscope for the generation of the second image data.

The processing module 114 is configured to generate the image output signal for the display 130 of the microscope system. In general, the display 130 of the microscope system may be any display, e.g., an auxiliary display that is used in addition to an ocular of the microscope system. For example, the microscope system may be a surgical microscope system. In this case, the display 130 may be a display that is attached to a base unit of the microscope system, or a display that is arranged in proximity of the eyepiece (ocular) of the microscope system (i.e., at the surgical microscope of the surgical microscope system). In some embodiments, the microscope system may be a laboratory microscope system. In this case, the auxiliary display may be a display that is (physically or logically) coupled to the microscope system, in addition to the eyepiece of the laboratory microscope.

In at least some embodiments, however, the display 130 may be an ocular display of an eyepiece of the microscope system. In other words, the display 130 may be integrated within the eyepiece (i.e., ocular) of the microscope system. In general, the display 130 may be used to display the magnified field of view of the microscope system to a user (such as the surgeon) of the microscope system. In addition, auxiliary information may be displayed on the display, e.g., based on the image output signal.

In at least some embodiments, the image output signal may comprise, or be based on, the second image data. In other words, the image output signal may show the second image data. In addition, the image output signal may comprise, or be based on, auxiliary information, such as the first image data or information that is to be overlaid over the second image data. In any case, the second image data might always be shown on the display, and the auxiliary information might be shown in some cases, e.g., upon request of a user of the microscope system, or in case an abnormality is found outside the second field of view.

Accordingly, in some embodiments, an overview of the first image data is overlaid over the second image data within the image output signal. In other words, the processing module may be configured to generate the image output signal such, that the first image data is overlaid over the second image data within the image output signal. Examples of such embodiments can be seen in FIGS. 3a to 3c, for example, where the second image data is denoted by 312, and the overview of the first image data is denoted by 314. The image output signal may be configured to cause the display to show the first image data as an overlay over the second image data. In some embodiments, the first image data may (temporarily) cover all or at least 60% (or at least 70%, at least 80%, at least 90%) of a display area of the display 130. In other words, the first image data may (temporarily, approximately) displace the second image data within the display area of the display 130, or the first image data may be superimposed over the second image data within the display area of the display 130. Alternatively or additionally, the first image data may be (temporarily) overlaid (i.e., superimposed) over a smaller portion of the second image data. For example, the first image data may be (temporarily) overlaid (i.e., superimposed) over at least 5% (or at least 10%) of the display area of the display 130, and/or at most 30% (or at most 25%, at most 20%, at most 15%) of the display area of the display 130. For example, the first image data may be overlaid over the second image data outside a central area of the second image data, i.e., offset towards a peripheral area of the second image data. In some embodiments, the processing module may be configured to process the second image data to detect a portion of the second image data that is of less interest than other portions of the second image data (e.g., based on a use of surgical instruments visible within the second image data, or based on features of the sample that are visible within the second image data), and to overlay the first image data over the portion of the second image data that is of less interest.

In some embodiments, the spatial relationship between the first and the second image data may be shown on the display. For example, as shown in FIG. 3b, a location of the second field of view within the first field of view may be highlighted within the overview of the first image data. In other words, the location of the second field of view may be overlaid over the overview of the first image data. For example, the location of the second field of view may be shown as a geometric form, such as an ellipse/circle or a rectangle within the overview of the first image data.

As mentioned before, and as shown in FIGS. 3a to 3d, the sample may be a sample of organic tissue of a surgical site. Accordingly, the first image data may comprise an overview of the surgical site. For example, the first image data may show the entire surgical site, or a portion of the surgical site comprising the second field of view. The second image data may comprise a magnified view of a portion of the surgical site (which is also shown by the first image data). The overview of the surgical site may be overlaid over a portion of the magnified view. In other words, the overview of the surgical site (i.e., the first image data) may be overlaid over a portion of the magnified view (i.e., the second image data) within the image output signal.

In some embodiments, the first image data may be processed to detect incidents that occur outside the second field of view, e.g., in order to alert the user/surgeon of the incident while the user concentrates on the second field of view. These incidents may vary—for example, in surgical microscopes, a bleeding that is only visible outside the second field of view may be such an incident, or the actions of another surgeon that assists the primary surgeon that operates the surgical microscope. Such incidents may also be denoted "abnormalities", since they deviate from the norm of there being no incidents. Accordingly, the processing module may be configured to process the first image data to detect an abnormality outside the second field of view. For example, the first image data may be processed using an image processing algorithm or using a machine-learning model/artificial intelligence in order to detect the abnormality. For example, the machine-learning model may be trained to detect abnormalities within image data, e.g., to detect an occurrence and/or a location of an abnormality, such as bleeding, within the image data. For example, as hinted above, the processing module may be configured to detect bleeding outside the second field of view. In this case, information on the bleeding may be overlaid over the second image data, e.g., as shown in FIGS. 3c and 3d. For example, a visual indicator, such as a pictogram, an arrow, a discoloration, a blinking effect, or text (such as a text alert 336 of FIGS. 3c and 3d), may be overlaid over the second image data as information on the bleeding. In some embodiments, information on a location of the bleeding is overlaid over the second image data, e.g., as overlay at a side of the second image data that indicates the location of the irregularity relative to the second field of view, e.g., as shown by arrows 334 and 342 of FIGS. 3c and 3d, or by rectangle 332 of FIG. 3c. For example, the information on the bleeding may be overlaid over a portion of the second image data that indicates the location of the bleeding. For example, if the bleeding is located at the right relative to the second field of view, the information on the bleeding may be overlaid at the right side of the second image data etc. Alternatively or additionally, the location of the bleeding may be highlighted within the overview of the surgical site, e.g., as shown by rectangle 332 of FIG. 3c. In other words, the overview of the surgical site may be overlaid over a portion of the magnified view (i.e., the second image data) within the image output signal upon detection of the bleeding. The location of the bleeding may be highlighted within the overview of the surgical site. In more general terms, an overview of the first image data may be overlaid over the second image data if an abnormality is detected outside the second field of view. A location of the abnormality may be highlighted in the overview of the first image data.

Embodiments of the present disclosure may also be used in other fields outside the medical fields. For example, embodiments may be used in material testing. Accordingly, the sample may be a sample of material to be inspected. In material testing, often, spot checks are performed to observe the material at random or pre-defined points of the surface of the sample. In some systems, other points of the sample are ignored. In embodiments, however, the first image data may be processed in order to detect abnormalities outside the locations used for the spot checks. In other words, the processing module may be configured to detect an irregularity (which is an abnormality) within the material outside the second field of view. For example, the processing module may be configured to detect the irregularity by comparing the first image data to reference image data suitable for the material at hand. The irregularity may be detected if a deviation between the first image data and the reference image data is larger than a threshold. In some embodiments, the reference image data may be based on previous first image data, i.e., the processing module may be configured to generate the reference image data based on the previous first image data. Information on the irregularity may be overlaid over the second image data (i.e., upon detection of an irregularity), e.g., as a pictogram, text, a blinking effect or a discoloration of the information shown on the display. Again, information on the location of the irregularity may be overlaid over the second image data, e.g., as part of the overview of the first image data, or as overlay at a side of the second image data that indicates the location of the irregularity relative to the second field of view.

In general, embodiments are not limited to two sources of image data. For example, an arbitrary number of optical imaging modules may be used to generate image data, which may be processed in order to detect abnormalities. In other words, the interface may be suitable for obtaining further image data from one or more further optical imaging modules (in addition to the first and second optical imaging modules). For example, the one or more further optical imaging modules may be arranged external to the microscope and may provide one or more additional fields of view on the sample or of a room comprising the microscope system (e.g., an operating room). The processing module may be configured to detect an abnormality within the further image data. Information on the abnormality within the further image data may be overlaid over the second image data within the image output signal, e.g., similar to the overlay of the information on the abnormality within the first image data.

In some embodiments, the user/surgeon might prefer to only show the overlay on demand. In other words, the overlay (of the information on the abnormality, or of the first image data) might only be shown when triggered by the user/surgeon of the microscope system. This trigger may be obtained via an input device 140 of the microscope system. Accordingly, the interface 112 may be suitable for obtaining a trigger signal from an input device 140 of the microscope system. For example, the input device may be one of a button, a touch-based interface (such as a touchscreen or a capacitive switch), a light-based input device (e.g., by blocking a path between light source and receiver, the input device is actuated), an ultrasound-based input device (e.g., by bringing a hand or object close to the ultrasound-based input device, the input device is actuated), and a voice-activated input device. The processing module may be configured to generate the image output signal such that the overview of the first image data or the information on the abnormality is overlaid over the second image data within the image output signal in response to the trigger signal of the input device. For example, the processing module may be configured to generate the image output signal such that the overview of the first image data or the information on the abnormality is overlaid over the second image data within the image output signal only if and/or as long the trigger signal is obtained from the input device.

In some embodiments, the first and second image data may also be used to illustrate a control of the microscope system. Many microscope systems, such as many surgical microscope systems, have a robotic adjustment system, such as a robotic arm, for positioning the microscope of the microscope system relative to a sample to be observed using the microscope system. The robotic adjustment system may be configured to adjust an arm of the microscope system in order to move the microscope relative to the sample. For example, the robotic adjustment system may be a robotic arm of the (surgical) microscope system. When the robotic adjustment system is used, the first and second image data may be used to illustrate the change in position of the microscope, and the corresponding change in the first and/or second field of view. This change in position may be triggered by a steering signal. Accordingly, the interface 112 may be suitable for (or configured to) obtaining/obtain a steering signal from an input device 140 of the microscope system (e.g., the input device as described above). Furthermore, the interface may be suitable for (e.g., configured to) providing/provide a control signal for a robotic adjustment system 150 of the microscope system. The processing module may be configured to control the robotic adjustment system based on the steering signal. In other words, the steering signal may indicate the direction, in which the microscope is to be moved, and the processing module may use the steering signal to generate a corresponding control signal for the robotic adjustment system, which may be configured to instruct the robotic adjustment system to move the microscope to the desired position. The moving of the microscope may affect a change in the field of view of the first and/or the second field of view. A change of the location of the second field of view within the (i.e., relative to) first field of view may be highlighted within the overview of the first image data (by the processing module). In other words, the processing module may be configured to indicate the change of the location of the second field of view relative to the first field of view within the image output signal.

The processing module 114 is further configured to provide the image output signal to the display 130. In other words, the processing module 114 may be configured to transmit the image output signal to the display 130, e.g., in order to supply the display 130 with the image output signal.

The interface 112 may correspond to one or more inputs and/or outputs for receiving and/or transmitting information, which may be in digital (bit) values according to a specified code, within a module, between modules or between modules of different entities. For example, the interface 112 may comprise interface circuitry configured to receive and/or transmit information. In embodiments the processing module 114 may be implemented using one or more processing units, one or more processing devices, any means for processing, such as a processor, a computer or a programmable hardware component being operable with accordingly adapted software. In other words, the described function of the processing module 114 may as well be implemented in software, which is then executed on one or more programmable hardware components. Such hardware components may comprise a general-purpose processor, a Digital Signal Processor (DSP), a micro-controller, etc.

More details and aspects of the microscope system or the apparatus for the microscope system are mentioned in connection with the proposed concept or one or more examples described above or below (e.g., FIGS. 2a to 4). The microscope system or the apparatus for the microscope system may comprise one or more additional optional features corresponding to one or more aspects of the proposed concept or one or more examples described above or below.

Figure 2A:
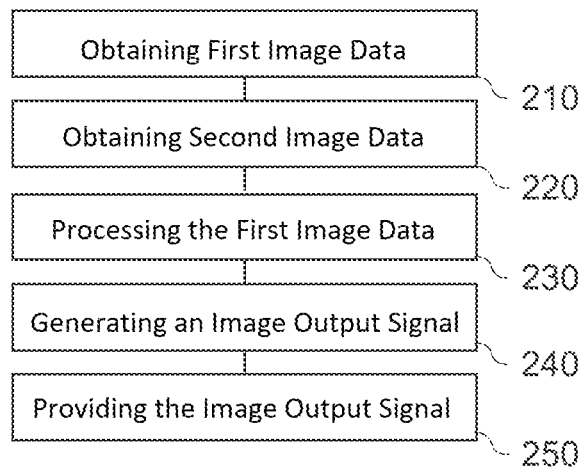
FIG. 2a shows a flow chart of an embodiment of a method for a microscope system.

FIG. 2a shows a flow chart of an embodiment of a (corresponding) method for a microscope system. For example, the microscope system may be implemented similar to the microscope system of FIG. 1b. The method comprises obtaining 210 first image data of a sample from a first optical imaging module. The first image data has a first field of view. The method comprises obtaining 220 second image data of the sample from a second optical imaging module. The second image data has a second field of view. The first field of view comprises the second field of view. The embodiment of the method comprises processing 230 the first image data to detect an abnormality outside the second field of view. The embodiment of the method comprises generating 240 an image output signal for a display 130 of the microscope system. Information on the abnormality is overlaid over the second image data within the image output signal. The method comprises providing 250 the image output signal to the display.

As indicated above, features described in connection with the apparatus 110 and the microscope system 100 of FIGS. 1a and/or 1b may be likewise applied to the method of FIG. 2a.

More details and aspects of the method are mentioned in connection with the proposed concept or one or more examples described above or below (e.g., FIG. 1a to 1b, 2b to 4). The method may comprise one or more additional optional features corresponding to one or more aspects of the proposed concept or one or more examples described above or below.

Figure 2B:
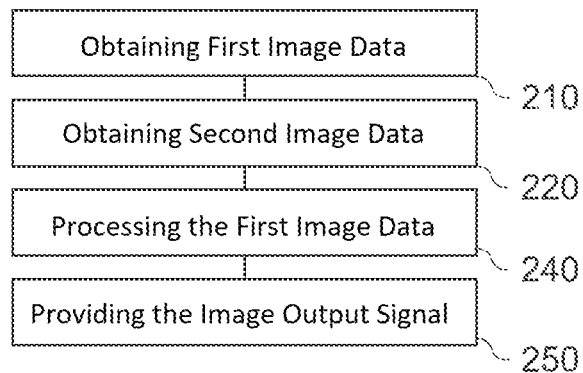
FIG. 2b shows a flow chart of another embodiment of a method for a microscope system.

FIG. 2b shows a flow chart of another embodiment of the (corresponding) method for a microscope system. For example, the microscope system may be implemented similar to the microscope system of FIG. 1b. The method comprises obtaining 210 first image data of a sample from a first optical imaging module. The first image data has a first field of view. The method comprises obtaining 220 second image data of the sample from a second optical imaging module. The second image data has a second field of view, the first field of view comprising the second field of view. The method comprises generating 240 an image output signal for a display 130 of the microscope system. An overview of the first image data is overlaid over the second image data within the image output signal. The method comprises providing 250 the image output signal to the display.

As indicated above, features described in connection with the apparatus 110 and the microscope system 100 of FIGS. 1a and/or 1b may be likewise applied to the method of FIG. 2b.

More details and aspects of the method are mentioned in connection with the proposed concept or one or more examples described above or below (e.g., FIG. 1a to 2a, 3a to 4). The method may comprise one or more additional optional features corresponding to one or more aspects of the proposed concept or one or more examples described above or below.

Observation through the microscope eyepiece, which provides a high magnification image of a very narrow field of view, may lead to a detriment of awareness over the broader surgical cavity (i.e., the surgical site), and the patient overall. This may, in some cases, lead to a delayed recognition of incidents outside the magnified field of view. On the other hand, the surgeon may remove the eyes from the eyepiece and look with naked eyes, but this may be detrimental to the focus, and might not be performed as often as desired.

Embodiments may use a secondary camera with a wide field of view (FOV, e.g., the first field of view) to offer awareness about the patient. For example, this secondary image (i.e., the first image data) may be displayed digitally in the eyepiece or on any other display (of the microscope system). For example, the secondary image may be displayed per request, e.g., while a button is pushed, or continuously as picture-in-picture (as an overlay). For example, AI (Artificial Intelligence) or other image processing algorithms may analyze the image in real time and provide warning in certain events (e.g., upon detection of an abnormality), such as bleeding. For example, the wide FOV image (i.e., the first image data) may be used to provide the overview of the surgical cavity (i.e., of the first field of view), and the exact location of the microscope view (i.e., the second field of view), like a mini overview map in computer games. The overview map may be used to control the area imaged by the microscope, using the robotic functionality (i.e., the robotic adjustment system) of the microscope. Additional external cameras (e.g., the one or more further optical imaging modules) may capture other views such as surgical spot wide field, and 360° camera for Operating Room awareness.

More details and aspects of the microscope system are mentioned in connection with the proposed concept or one or more examples described above or below (e.g., FIG. 1a to 4). The microscope system may comprise one or more additional optional features corresponding to one or more aspects of the proposed concept or one or more examples described above or below.

Figure 3A:
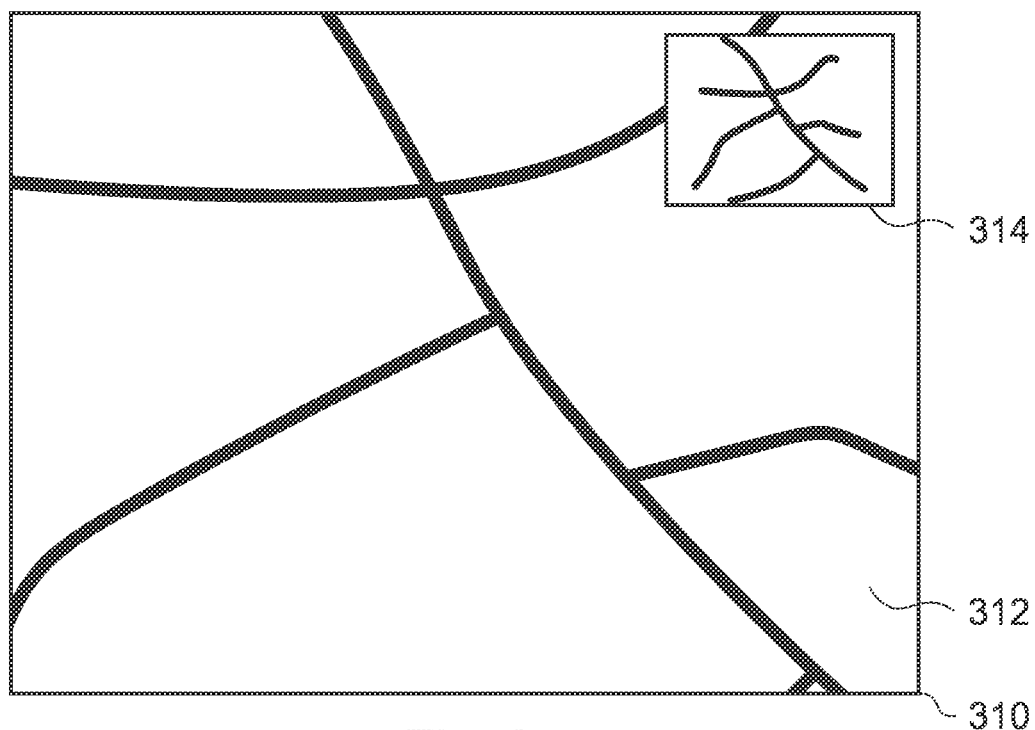
FIGS. 3a to 3d show examples of an output of a display for different types of image output signals.
Figure 3B:
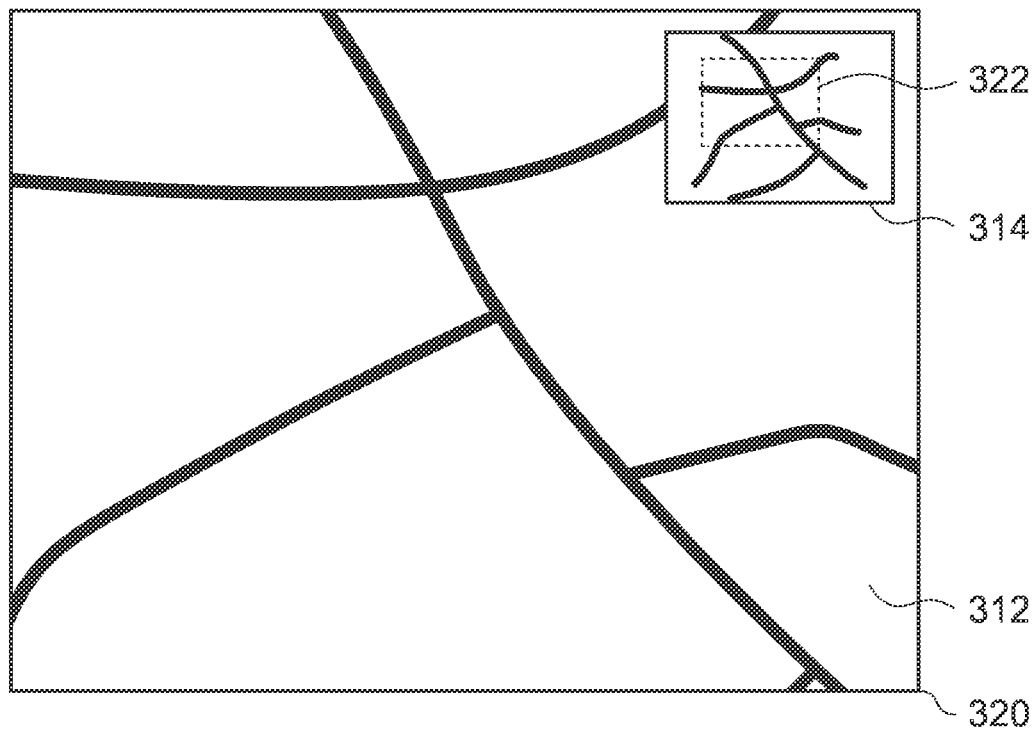
Figure 3C:
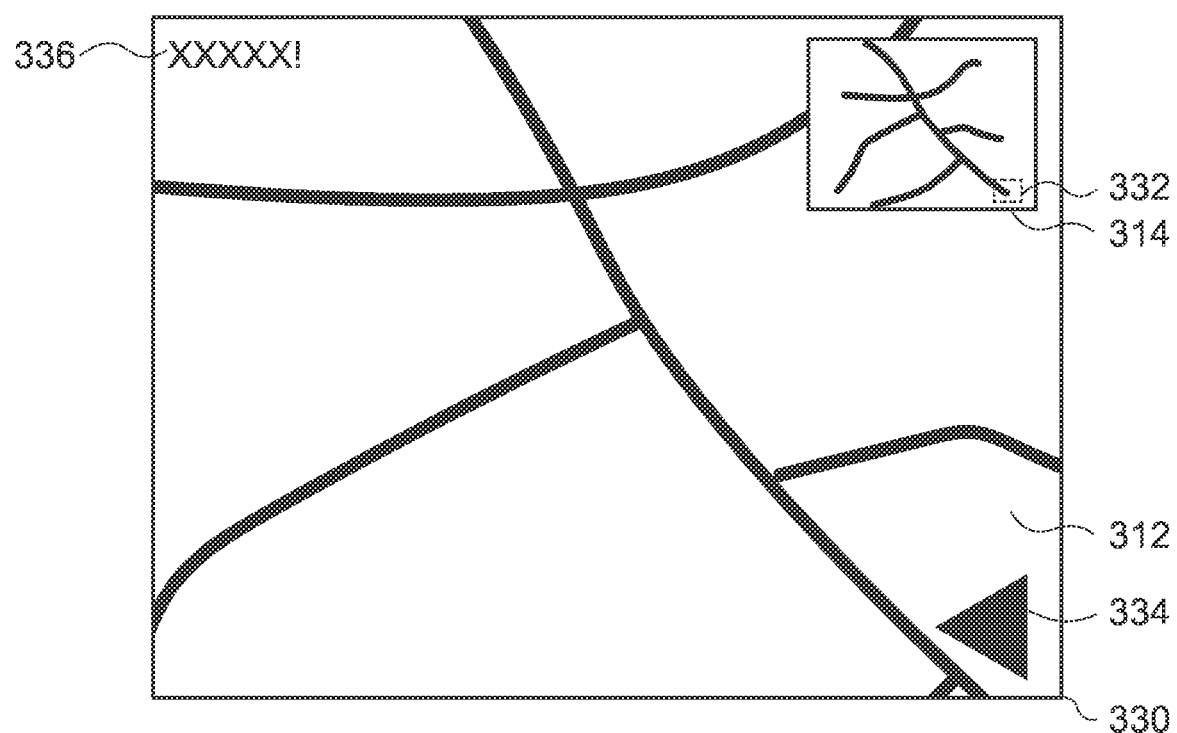
Figure 3D:
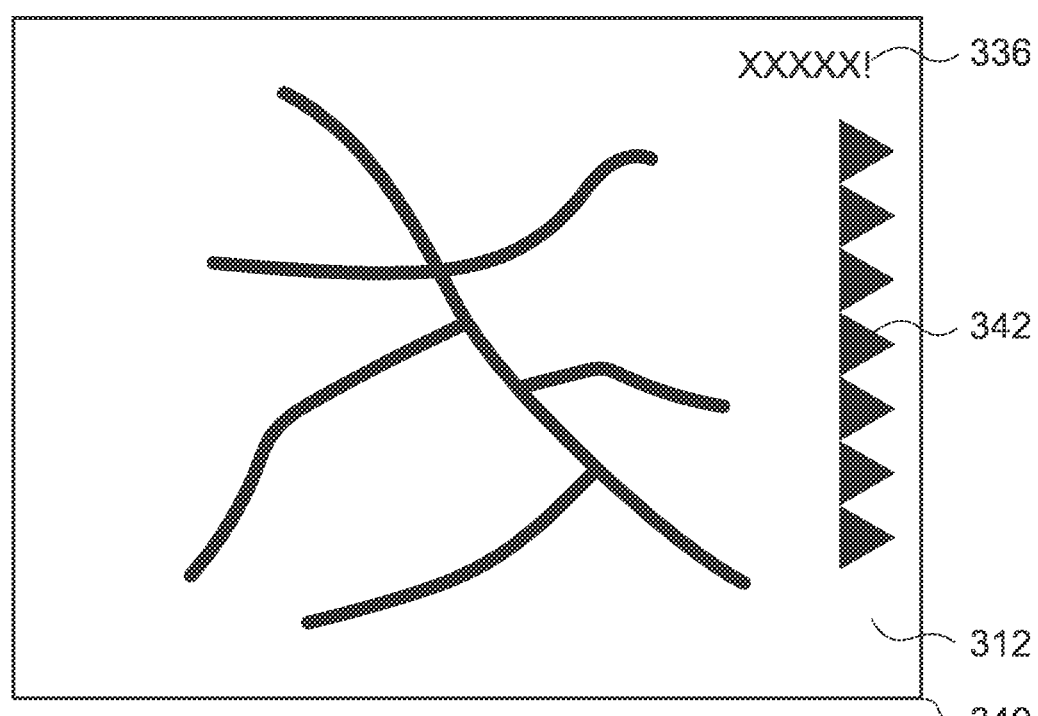

FIGS. 3a to 3d show examples of an output of a display for different types of image output signals. In FIGS. 3a to 3d, image data of a surgical site is shown. In FIG. 3a, an output 310 of a display is shown, wherein an overview of first image data 314 is overlaid over second image data 312. In FIG. 3a (and FIGS. 3b and 3c), the first image data shows a field of view that comprises the field of view of the second image data. In some embodiments, information on an abnormality may be shown in the overview of the first image data. In FIG. 3b, an output 320 of a display is shown, wherein a position 322 of the second image data relative to the first image data is highlighted within the overview of the first image data. In FIG. 3c, an output 330 of a display is shown, wherein another portion 332 of the first image data is highlighted, to highlight a location of an abnormality. Additionally, and optionally, in FIG. 3c, an arrow 334 is shown indication a location of the abnormality relative to the second field of view, and/or a text alert 336 is shown to alert the user, e.g., to alert a surgeon of a bleeding. In FIG. 3d, an output 340 of a display is shown, wherein the first image data is not shown overlaid over the first image data. Instead, the information on the abnormality is shown as arrows indicating a location of the abnormality relative to the second field of view.

More details and aspects of the examples are mentioned in connection with the proposed concept or one or more examples described above or below (e.g., FIG. 1a to 2b, 4). The microscope system may comprise one or more additional optional features corresponding to one or more aspects of the proposed concept or one or more examples described above or below.

Figure 4:
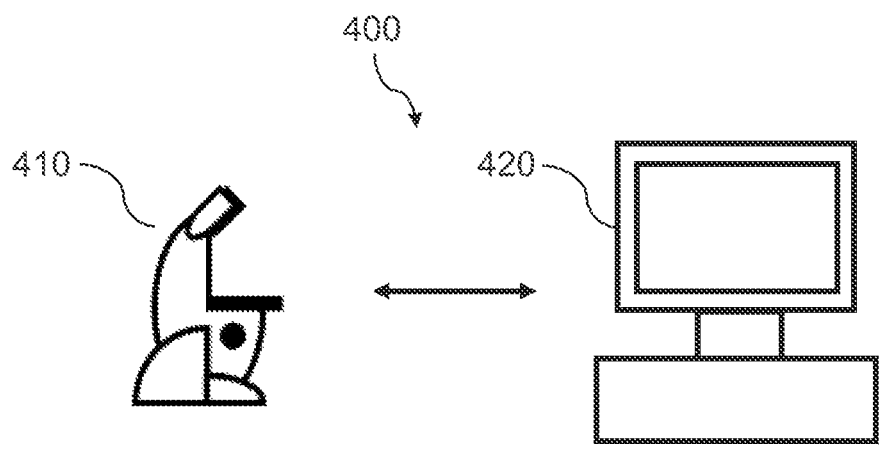
FIG. 4 shows a schematic diagram of a system comprising a microscope and a computer system.

FIG. 4 shows a schematic diagram of a system comprising a microscope and a computer system. Some embodiments relate to a microscope comprising a system as described in connection with one or more of the FIGS. 1 to 3d. Alternatively, a microscope may be part of or connected to a system as described in connection with one or more of the FIGS. 1 to 3d. FIG. 4 shows a schematic illustration of a system 400 configured to perform a method described herein. The system 400 comprises a microscope 410 and a computer system 420. The microscope 410 is configured to take images and is connected to the computer system 420. The computer system 420 is configured to execute at least a part of a method described herein. For example, the computer system may implement the apparatus 110. The computer system 420 may be configured to execute a machine learning algorithm. The computer system 420 and microscope 410 may be separate entities but can also be integrated together in one common housing. The computer system 420 may be part of a central processing system of the microscope 410 and/or the computer system 420 may be part of a subcomponent of the microscope 410, such as a sensor, an actor, a camera or an illumination unit, etc. of the microscope 410.

The computer system 420 may be a local computer device (e.g., personal computer, laptop, tablet computer or mobile phone) with one or more processors and one or more storage devices or may be a distributed computer system (e.g., a cloud computing system with one or more processors and one or more storage devices distributed at various locations, for example, at a local client and/or one or more remote server farms and/or data centers). The computer system 420 may comprise any circuit or combination of circuits. In one embodiment, the computer system 420 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g., camera) or any other type of processor or processing circuit. Other types of circuits that may be included in the computer system 420 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 420 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 420 may also include a display device, one or more speakers, and a keyboard and/or controller, which can include a mouse, trackball, touch screen, voice-recognition device, or any other device that permits a system user to input information into and receive information from the computer system 420.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g., words or sentences) and associated training content information (e.g., labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g., sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e., each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g., a classification algorithm, a regression algorithm or a similarity learning algorithm. Classification algorithms may be used when the outputs are restricted to a limited set of values (categorical variables), i.e., the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning, (only) input data might be supplied and an unsupervised learning algorithm may be used to find structure in the input data (e.g., by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input but also transform it in a way that makes it useful, often as a pre-processing step before performing classification or predictions. Feature learning may be based on principal components analysis or cluster analysis, for example.

In some examples, anomaly detection (i.e., outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g., a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g., be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge (e.g., based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g., of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e., to achieve a desired output for a given input.

Alternatively, the machine-learning model may be a support vector machine, a random forest model or a gradient boosting model. Support vector machines (i.e., support vector networks) are supervised learning models with associated learning algorithms that may be used to analyze data (e.g., in classification or regression analysis). Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

LIST OF REFERENCE SIGNS

100 Microscope system
110 Apparatus
112 Interface
114 Processing module
120a First optical imaging module
120b Second optical imaging module
130 Display
140 Input device
150 Robotic adjustment system
210 Obtaining first image data
220 Obtaining second image data
230 Processing the first image data
240 Generating an image output signal
250 Providing the image output signal
310 Output of a display
312 Second image data
314 Overview of first image data
320 Output of a display
322 Location of second image data
330 Output of a display
332 Location of abnormality
334 Arrow indicating location of abnormality
336 Text alert
340 Output of a display
342 Arrows indicating location of abnormality
400 System
410 Microscope
420 Computer system

What is claimed is:

1. An apparatus for a microscope system, the apparatus comprising:
an interface for:
obtaining first image data of a sample from a first optical imaging module, the first image data having a first field of view,
wherein the sample is a sample of organic tissue of a surgical site, and obtaining second image data of the sample from a second optical imaging module, the second image data having a second field of view,
wherein the first field of view comprises the second field of view; and
a processing module configured to:
process the first image data to detect an abnormality outside the second field of view by comparing the first image data to a reference image data,
wherein the reference image data is generated based on a previous first image data,
wherein the abnormality is detected if a deviation between the first image data and the reference image data is larger than a threshold,
generate an image output signal for a display of the microscope system, wherein information on the abnormality is overlaid over the second image data within the image output signal,
wherein an overview of the first image data is overlaid over the second image data if the abnormality is detected outside the second field of view, wherein the overview indicates a location of the abnormality detected outside the second field of view, and
provide the image output signal to the display.

2. The apparatus according to claim 1, wherein the display is an ocular display of an eyepiece of the microscope system.

3. The apparatus according to claim 1, wherein the abnormality detected by the processing module is a bleeding and wherein information on a location of the bleeding is overlaid over the second image data.

4. The apparatus according to claim 1, wherein a position of the overlaid information indicates a location of the abnormality relative to the second image data.

5. The apparatus according to claim 1, wherein a location of the abnormality is highlighted in the overview of the first image data.

6. The apparatus according to claim 1, wherein:
the interface is suitable for obtaining further image data from one or more further optical imaging modules,
the processing module is configured to detect the abnormality within the further image data, and
information on the abnormality within the further image data is overlaid over the second image data within the image output signal.

7. An apparatus for a microscope system for performing materials inspection, the apparatus comprising:
an interface for:

obtaining first image data of a sample from a first optical imaging module, the first image data having a first field of view of an inspection spot,
wherein the sample is of a material to be inspected, and
obtaining second image data of the sample from a second optical imaging module, the second image data having a second field of view,
wherein the first field of view comprises the second field of view; and
a processing module configured to:
process the first image data to detect an irregularity within the sample of material outside the second field of view by comparing the first image data to a reference image data suitable for the material,
wherein the irregularity is detected if a deviation between the first image data and the reference image data is larger than a threshold,
generate an image output signal for a display of the microscope system, wherein information on the irregularity is overlaid over the second image data within the image output signal,
wherein an overview of the first image data is overlaid over the second image data if the irregularity is detected outside the second field of view, wherein the overview indicates a location of the irregularity detected outside the second field of view, and
provide the image output signal to the display.

8. The apparatus according to claim 7, wherein:
the interface is suitable for obtaining a trigger signal from an input device of the microscope system, and
the processing module is configured to generate the image output signal such that:
the overview of the first image data is overlaid over the second image data within the image output signal in response to the trigger signal of the input device, and/or
a location of the second field of view within the first field of view is highlighted within the overview of the first image data.

9. The apparatus according to claim 8, wherein:
the interface is suitable for obtaining a steering signal from an input device of the microscope system and for providing a control signal for a robotic adjustment system of the microscope system,
the processing module is configured to control the robotic adjustment system based on the steering signal, and
a change of the location of the second field of view within the first field of view is highlighted within the overview of the first image data.

10. The apparatus according to claim 7, wherein the processing module is further configured to generate the reference image data based on a previous first image data.

11. A method for a microscope system, the method comprising:
obtaining first image data of a sample from a first optical imaging module, the first image data having a first field of view,
wherein the sample is a sample of organic tissue of a surgical site;
obtaining second image data of the sample from a second optical imaging module, the second image data having a second field of view, the first field of view comprising the second field of view;
processing the first image data to detect an abnormality outside the second field of view by comparing the first image data to a reference image data,
wherein the reference image data is generated based on a previous first image data,
wherein the abnormality is detected if a deviation between the first image data and the reference image data is larger than a threshold;
generating an image output signal for a display of the microscope system,
wherein information on the abnormality is overlaid over the second image data within the image output signal,
wherein an overview of the first image data is overlaid over the second image data if the abnormality is detected outside the second field of view, wherein the overview indicates a location of the abnormality detected outside the second field of view; and
providing the image output signal to the display.

12. A method for a microscope system for performing materials inspection, the method comprising:
obtaining first image data of a sample from a first optical imaging module, the first image data having a first field of view of an inspection spot,
wherein the sample is of a material to be inspected;
obtaining second image data of the sample from a second optical imaging module, the second image data having a second field of view, the first field of view comprising the second field of view;
processing the first image data to detect an irregularity within the sample of material outside the second field of view by comparing the first image data to a reference image data suitable for the material,
wherein the irregularity is detected if a deviation between the first image data and the reference image data is larger than a threshold;
generating an image output signal for a display of the microscope system,
wherein information on the irregularity is overlaid over the second image data within the image output signal,
wherein an overview of the first image data is overlaid over the second image data if the irregularity is detected outside the second field of view, wherein the overview indicates a location of the irregularity detected outside the second field of view; and
providing the image output signal to the display.

13. The method according to claim 12, further comprising generating the reference image data based on a previous first image data.

14. A non-transitory, computer-readable medium storing a program code for performing the method of claim 11 when the program code is executed on a processor.

15. A non-transitory, computer-readable medium storing a program code for performing the method of claim 12 when the program code is executed on a processor.

* * * * *